(12) United States Patent
Karlsson-Parra et al.

(10) Patent No.: US 8,673,296 B2
(45) Date of Patent: Mar. 18, 2014

(54) METHOD AND COMPOSITION FOR PRODUCING A CELLULAR ALLOGENEIC VACCINE

(75) Inventors: Alex Karlsson-Parra, Molndal (SE); AnnaCarin Wallgren, Molndal (SE); Bengt Andersson, Molndal (SE)

(73) Assignee: Immunicum AB, Gothenburg (SE)

( * ) Notice: Subject to any disclaimer, the term of this patent is extended or adjusted under 35 U.S.C. 154(b) by 197 days.

(21) Appl. No.: 11/603,819

(22) Filed: Nov. 24, 2006

(65) Prior Publication Data

US 2007/0134219 A1    Jun. 14, 2007

Related U.S. Application Data

(62) Division of application No. 10/516,915, filed as application No. PCT/SE03/00936 on Jun. 5, 2003, now abandoned.

(60) Provisional application No. 60/385,898, filed on Jun. 6, 2002.

(30) Foreign Application Priority Data

Jun. 6, 2002    (SE) ...................................... 0201726

(51) Int. Cl.
| | | |
|---|---|---|
| A01N 63/00 | (2006.01) | |
| A61K 45/00 | (2006.01) | |
| A61K 47/00 | (2006.01) | |

(52) U.S. Cl.
USPC ..................... 424/93.71; 424/278.1

(58) Field of Classification Search
None
See application file for complete search history.

(56) References Cited

U.S. PATENT DOCUMENTS

| | | | |
|---|---|---|---|
| 5,788,963 A * | 8/1998 | Murphy et al. ............ | 424/93.21 |
| 5,985,270 A | 11/1999 | Srivastava | |
| 6,251,665 B1 | 6/2001 | Cezayirli et al. | |
| 2002/0025320 A1 | 2/2002 | Boyaka et al. | |
| 2002/0039583 A1 | 4/2002 | Subjeck et al. | |
| 2003/0039653 A1* | 2/2003 | Chen et al. ................. | 424/155.1 |

FOREIGN PATENT DOCUMENTS

| | | |
|---|---|---|
| WO | WO 94/21798 | 9/1994 |
| WO | WO 9833527 A2 * | 8/1998 |
| WO | 99/47687 | 9/1999 |

OTHER PUBLICATIONS

Nair et al., 1997, Int. J. Cancer, vol. 70: 706-715.*
Nouri-Shirazi et a., 2000, Immunol. Letters. vol. 74: 5-10.*
Heiser et al., J. Immunol, 2001, vol. 166: 2953-2960.*
Williams et al., 2007, Immunol. vol. 124: 89-101.*
Merrick et al., 2008, Canc. Immunol. Immuonther. vol. 57: 897-906.*
Rios et al., 1972, Canc. Res. vol. 32: 16-21.*
Ashley et al., 1997, J. Neuroimmunol. vol. 78: 34-46.*
Int. J. Cancer, vol. 86, 2000, Edwin Y. Chang et al, "Antigen-Specific Cancer Immunotheraphy Using a GM-CSF Secreting Allogeneic Tumor Cell-Based Vaccine", p. 725, col. 2, line 24—p. 726, col. 1, line 27, abstract.
The Journal of Immunology, vol. 162, 1999, Silvia Corinti et al, "Cross-Linking of Membrande CD43 Mediates Dendritic Cell Maturation", p. 6331—p. 6336, abstract, p. 6335, lines 1-5, col. 1.
Oh et al, Viral Neruaminidase treatment of dendritic cells enhances antigen-specific CD8 T cell proliferation but doesnot account for the CD4 T cell independence of the CD8 T cell response during influensa virus infection. 2001. Virology vol. 286:403-411.
Rees et al., 1991, Stress induced modulation of anitgen-presenting cell function. Immunology. vol. 74:386-392.
Weiss, 1966, The effecto of neuraminidase on the phagocytic process in human monocytes. Laboratory Investigation, vol. 15:1304-1309.
Fanales-Belasio et al., 1997, Antibodies against sialophorin (CD43) enhance the capapcity of dendritics cells to cluster to cluster and activate T lymphocytes J. Immunol., vol. 159:2203-2211.
Fields et al., 1998, Murine dendritic cells pulsed with whole tumor lysates mediate potent antitumor immune response in vitro and in vivo. PNAS vol. 95:9482-9487.
Selma Alijagic et al., "Dendritic cells generated from peripheral blood transfected with human tyrosinase induce specific T cell activation", Eur. J. Immunol., 1995, pp. 3100-3107, vol. 25, VCH Verlagsgesellschaft mbH, Weinheim, Germany.
Madhusudan V. Peshwa et al., "Generation of Primary Peptide-Specific CD8+Cytotoxic T-Lymphocytes in Vitro Using Allogenic Dendritic Cells", Cell Transplantation, 1998, pp. 1-9, vol. 7, No. 1, Elsevier Science Inc., USA.

* cited by examiner

*Primary Examiner* — Amy Juedes
(74) *Attorney, Agent, or Firm* — Harness, Dickey & Pierce, P.L.C.

(57) ABSTRACT

The present invention relates to a method for the production of a cellular allogeneic vaccine, which is based upon an allogeneic APC, comprising the following steps:
  isolation of an APC from a subject or providing an APC already established and/or isolated from a myeloid leukemia cell line, and
  modifying the APC with an antigen using any of the following methods: pulsing, transfection, infection or fusion;
  treatment using an agent capable of removing sialic acid on cell surfaces; and optionally
  culturing the APC in a suitable medium,
  an allogeneic vaccine obtainable by the above method, a composition comprising said vaccine and a pharmaceutically acceptable carrier and therapeutic use of said vaccine or said composition.

20 Claims, 11 Drawing Sheets

METHOD AND COMPOSITION FOR PRODUCING A CELLULAR ALLOGENEIC VACCINE

This invention concerns the technical field of molecular immunology and medicine, in particular a new method for the obtaining of a cellular allogeneic vaccine based upon allogeneic antigen-presenting cells (APCs), preferably monocytes, compositions comprising said APCs and use of said APCs. The vaccine is preferably used for treatment of cancer.

BACKGROUND

During the first half of the 1990's many research groups worked departing from the hypothesis that autologous tumor cells (taken from the same human being) could be reformed to be potent antigen-presenting cells (APCs) through genetic modification. In vivo studies in mice were reported in which tumor cells, transfected ex vivo with genes coding for the co-stimulatory molecule B7, used as cancer vaccine by injecting these cells into the recipient had some success. The hypothesis was that the tumor cell not only would express signal 1 (MHC class I+tumor peptide) for CD8+ tumor specific T cells but also signal 2, B7, which theoretically could lead to an efficient activation of these tumor reactive CD 8+ CTL (cytotoxic T lymphocyte).

During a critical survey of the underlying immunological mechanisms responsible for the often very positive effects of such vaccination protocol, it was clearly shown that professional APCs of the host, rather than the vaccinating tumor cells themselves, were responsible for CTL priming. Most likely tumor cells expressing B7 were efficiently killed by natural killer (NK)-cells. This NK-cell mediated immune response has further been shown to induce a local recruitment of host antigen-presenting cells (APCs), including dendritic cells (DCs), whereby these cells take up whole cellular proteins released into the tumor's microenvironment and present them indirectly to CTL, so called cross-priming. This indirect pathway of antigen presentation also explain why vaccination with tumor cells transfected with the gene coding for granulocyte-macrophage colony stimulating factor (GM-CSF) induce a reasonably good anti-tumor response in rodent models since local GM-CSF production have been shown to induce a local production of macrophage inflammatory protein (MIP)-1 alpha which is a strong chemoattractant for DC-precursors such as monocytes and immature DC:s. It has moreover been shown that a local injection of a plasmide vaccine expressing GM-CSF induces a local accumulation of immature DCs at the vaccination site that is followed by the appearance of mature DCs in regional lymph nodes, consistent with egression of maturating DC from the injection site and migration to the draining lymph nodes. The indirect pathway of tumor antigen presentation also solves the problem with the demand for CD4+ T helper type-1 (Th1) cells in order to achieve an efficient and long-lasting tumor-specific CTL immune response since also MHC class II restricted CD4+ cells can be activated via the indirect pathway.

With this knowledge at hand it was now open for refining this principle, ex vivo and in vivo, which is based upon an efficient indirect presentation of tumor antigen by host (autologous) APC. An obvious approach has been to propagate potent APCs ex vivo, in particular dendritic cells (DCs), and thereupon load these cells with tumor-derived proteins either by pulsing or transfection. Also so called dendritoma vaccines, where autologous tumor cells have been fused with autologous monocyte-derived DCs, have been developed. A problem with ex vivo propagation of autologous DCs is however the minor migration of these cells to draining lymph nodes (a prerequisite for the injected DCs to meet naive T cells). Studies in humans have shown that 1% maximum of subcutanously injected DCs migrates to regional lymph nodes. An alternative approach has therefore been developed, above all from the observations during vaccination with GM-CSF producing tumor cells in rodent models, with the goal to induce an efficient recruitment in vivo of host DCs to the vaccination site. Phase I trials in humans with prostate and renal carcinoma and melanoma using autologous GM-CSF transfected tumor cells vaccines have been evaluated and found to be safe but without any obvious clinical effect. Additionally, a vaccine based upon autologous tumor cells have been shown to create several technical problems. Firstly, the vaccine depends on the availability of adequate numbers of tumor cells, which are rarely available because of the reactive process that are found infiltrating tumor cells of many common cancers. Secondly, the vaccine requires de novo gene transfer for treatment of each patient, which is labor intensive and may cause variable cytokine expression levels between different patient vaccines. Thirdly, there is significant expense and time required to certify each patient's lot of vaccine so that they meet accepted administration guidelines. One way to circumvent these technical obstacles is to use a vaccine strategy that is based on a panel of cytokine-expressing allogeneic tumor cell lines that can be formulated and stored before the initiation of clinical studies. This is a particularly attractive approach for the majority of common cancers for which specific tumor antigens have not yet been identified. Two findings provide the immunologic rationale for an allogeneic tumor-cell vaccine approach. Firstly, that DCs of the host, rather than the vaccinating tumor themselves, are responsible for priming of CD4+ cells and CD8+ CTL, both of which are required for generating systemic antitumor immunity (see above). Secondly, many tumor antigens are commonly expressed among different patient's tumors. A GM-CSF vaccine based on this concept has been developed in rodent models (Chang E. Y. et al, (International Journal of Cancer, 2000, Vol 86. No. 5, pp 725-730) and was recently studied in a Phase I trial and found to be safe but without any obvious clinical effect. Most likely, this clinical insufficiency was due to the production of one single cytokine (GM-CSF) since theoretically several factors ought to be produced locally in order to induce not only an efficient recruitment of immature DCs but also an efficient maturation of these cells. Necessary factors most probably include chemotactic cytokines such as MIP-1 alpha and/or RANTES, maturation factors such as interleukin (IL)-1 beta, IL-6 and/or tumor necrosis factor (TNF) alpha and finally Th1-polarizating factors such as interferon (IFN) gamma.

Within the transplantation and transfusion areas there is daily struggling with the problem of allo-immunization, which is a T-cell-mediated immunization against indirectly presented donor-specific HLA-antigens. Such immunization is frequently developed with a strong power after transfusions with allogeneic blood products and after transplantation of solid organs. Not even a powerful continuous immunosuppressive treatment after a primary successful transplantation of a HLA-incompatible organ appears to prevent a slowly progressing process referred to as chronic rejection. This process is mediated by CD4+ cells of Th1-type, which are activated by allogeneic HLA-peptides indirectly presented by autologous APCs. These CD4+ T cells in turn activate donor-specific antibody (IgG)-producing B-cells and cytotoxic T cells and tissue macrophages, which constitute the different effector mechanisms during chronic rejection. A very central actor for the starting-up of an allo-immunization appears to be viable, metabolically intact, donor-derived (allogeneic) APCs. If these are depleted or inactivated by UVB-irradiation before a transfusion of e.g. platelet concentrates then the immunization is usually avoided. This also pertain passenger APCs in transplanted tissue; if these allogeneic APCs are depleted before transplantation the risk for a subsequent immunization with chronic rejections is essentially decreased. For non-viable allogeneic tissue the same immunization rules pertains as for other foreign protein-derived antigens i.e. in order to achieve an essential immunization it is necessary to administer the antigen in a relatively large amount together with an adjuvant as e.g. Freuds complete adjuvant (FCA). The same is valid for in vitro primary stimulation with non-viable MHC-expressing allogeneic APCs or pure MHC-derived allo-peptides which do not induce any substantial priming of naive T cells indirectly recognizing allo-derived peptides. A substantial priming of these T cells is however obtained by using viable allogeneic MHC-expressing APC during the primary stimulation.

Something that differ (discriminates) primary stimulation with viable allogeneic APCs from primary stimulation with non-viable (lysed or apoptotic) allogeneic APCs in vitro is the very powerful T cell proliferation in the responder (host) cell population, only seen during stimulation with viable APCs. This reaction which is called allogeneic mixed leukocyte reaction (MLR) also leads to the production of certain chemokines and cytokines, including MIP-1 alpha, RANTES, IL-1beta, IL-6, TNF-alpha and IFN-gamma. The MLR is induced in both naive and memory responder T-cells that are cross-reacting with MHC molecules on allogeneic APCs through experiencing these molecules as their own MHC+ foreign peptide sequences which the T-cells that were predestined to react against. It has been shown that as many as 1 out of 20 of our circulating T cells may participate in this preformed allo-reactivity. It is further known that treatment of stimulator-APC with agents that reduce or remove sialic acids from glycoproteins on the cell membrane, such as neuraminidase and anti-CD43 antibodies, increase the potential of APC to induce a proliferative response in allogeneic T cells.

A method for inducing an antigen-specific immune response by co-administration of allogeneic DCs with autologous DC, in which the antigen was incorporated, to a subject is disclosed in WO 99/47687. The autologous DC were expected to present the antigen to CTLs while the allogeneic DC were expected to induce a strong reaction from alloreactive T cells resulting in the local release of stimulatory molecules that would amplify the ability of autologous DC to activate CTLs. No data supporting their hypothesis was presented nor any immune response elicited.

Vaccination with hybrid cells consisting of autologous tumor cells fused with allogeneic mature DC is described in "Regression of human metastatic cell carcinoma after vaccination with tumor cell-dendritic cell hybrids", A. Kugler et al. Nature Medicine, vol 6, No 3, March 2000, pp. 332-336. Theoretically, this method is based upon the expectance that co-expression of allogeneic MHC molecule on the semi-allogeneic tumor cell (expressing autologous MHC class I molecules+tumor peptides) would activate alloreactive T cells. This activation would result in a local release of stimulatory cytokines that would help to trigger the activation of CTLs recognizing the tumor peptide on autologous, tumor cell-derived, MHC class I molecules. Using this vaccine approach a limited number of patients with renal tumor exhibited a clinical anti-cancer response.

In WO 9421798 it is mentioned that transfection of DNA encoding neuraminidase protein into autologous APCs (but not allogeneic APCs) could be used to boost their ability to present tumor antigens directly to autologous, MHC-restricted, T cells (see page 3 line 20-23 and line 28, page 4 line 2 and page 7 line 22-26). This concept is based upon the central dogma within immunology put forward by Zinkernagl and Doherty in the middle of the 70's: A T-cell only recognize foreign peptides (e.g. tumor-derived peptides from an autologous or allogeneic tumor) if they are presented by APCs which express own MHC molecules (i.e MHC-compatible APC), so called "self MHC-restriction".

Methods utilizing the immunogenicity of allogneic APCs as adjuvant when vaccinating with antigen-loaded autologous APCs have earlier been disclosed as said above. In WO 99/47687, autologous antigen-loaded APC were expected to present the antigen to MHC-restricted autologous CTLs while the co-administered allogeneic APC were expected to induce an inflammatory allogeneic response that would amplify the ability of aotologous DC to activate CTLS.

A vaccine against other tumors, using dendritic cells fused with cancer cells, is also suggested in "Smallpox, polio and now a cancer vaccine?", D. W. Kufe, Nature Medicine, vol 6, No 3, March 2000, pp. 252-253. The methods of Kugler et al and Kufe above are however limited by a number of factors. Firstly, an autologous vaccine depends on the availability of adequate numbers of tumor cells, which are rarely available because of the reactive process that is found infiltrating tumor cells of many common cancers. Secondly, an autologous vaccine requires de novo gene transfer for treatment of each patient, which is labor intensive and may cause variable cytokine expression levels between different patient vaccines. Thirdly, there is significant expense and time required to certify each patient's lot of vaccine so that they meet accepted administration guidelines.

In US 20020039583 A1 there is further mentioned allogeneic and also xenogeneic APCs loaded with immune complex containing stress proteins as a thinkable cellular vaccine.

The methods disclosed in WO 99/47687 and in Nature Medicine by Kugler at al are however limited by a number of factors. First both methods are dependent on the availability of adequate numbers of autologous cells (APCs and/or tumor cells). Secondly, both methods require labour-intensive manipulations of autologous cells for treatment of each patient. Thirdly there is significant expense and time required to certify each patent's lot of vaccine so that they meet accepted administration guidelines.

Accordingly there is a need for a vaccine that creates a better immune.
response and is better suited for storing, producing in a large scale and is independent of supply limitations.

SUMMARY OF THE INVENTION

The present invention solves the above problems by providing, according to a first aspect a method for the production of a cellular allogeneic vaccine which is based upon an allogeneic APC, and comprising the following steps:

Isolation of an APC from a subject, preferably from a normal blood donor, or from a patient suffering from myeloid malignancies, or providing an APC already established and/or isolated from a myeloid leukemia cell line;

b) modifying the APC with an antigen using any of the following methods: pulsing, transfection, infection or fusion; and c) treatment of the APC with an agent capable of removing sialic acid from the surface of said APC; and optionally culturing the modified APC in a suitable medium. According to a second aspect, a cellular allogeneic vaccine obtainable by a method according to the first aspect is provided.

According to a third aspect, a composition comprising a vaccine according to the second aspect and a pharmaceutically acceptable carrier is provided. According to a fourth aspect, therapeutic use of a vaccine according to the second aspect or a composition according to the third aspect is provided.

DETAILED DESCRIPTION OF THE INVENTION

It is intended throughout the present description that the expression "cellular allogeneic vaccine" embraces any reagent, cell or compound capable of eliciting an antigen-specific immune response in a subject, wherein said reagent, cell or compound is of allogeneic origin i.e. originates from a donor, preferably a human donor, other than the recipient, preferably a human recipient, of the cellular allogeneic vaccine.

As used in the present specification and claims, the singular form "a", "an" and "the" include plural references unless the context clearly dictates otherwise. For example the term "a cell" includes a plurality of cells, including mixtures thereof.

The terms "antigen-presenting cell(s)", "APC" or "APCs" include both intact, whole cells as well as other molecules (all of allogeneic origin) which are capable of inducing the presentation of one or more antigens, preferably in association with class I MHC molecules, and all types of mononuclear cells which are capable of inducing an allogeneic immune response. Preferably whole viable cells are used as APCs. Examples of suitable APCs are discussed in detail below and include, but are not limited to, whole cells such as monocytes, macrophages, dendritic cells, monocyte-derived dendritic cells, macrophage-derived dendritic cells, B cells and myeloid leukaemia cells e.g. cell lines THP-1, U937, HL-60 or CEM-CM3. Myeloid leukaemia cells are said to provide so called pre-monocytes.

The terms "cancer," "neoplasm" and "tumor" used interchangeably and in either the singular or plural form, as appearing in the present specification and claims, refer to cells that have undergone a malignant transformation that makes them pathological to the host organism. Primary cancer cells (that is, cells obtained from near the site of malignant transformation) can be readily distinguished from non-cancerous cells by well-established techniques, particularly histological examination. The definition of a cancer cell, as used herein, includes not only a primary cancer cell, but also any cell derived from a cancer cell ancestor. This includes metastasized cancer cells, and in vitro cultures and cell lines derived from cancer cells. When referring to a type of cancer that normally manifests as a solid tumor, a "clinically detectable" tumor is one that is detectable on the basis of tumor mass; e.g., by such procedures as CAT scan, magnetic resonance imaging (MRI), X-ray, ultrasound or palpation. Biochemical or immunologic findings alone may be insufficient to meet this definition.

The term "genetically modified" means, as appearing in the present specification, containing and/or expressing a foreign gene or nucleic acid sequence which in turn, modifies the genotype or phenotype of the cell or its progeny. In other words, it refers to any addition, deletion or disruption to a cell's endogenous nucleotides. APCs modified using transfection, infection or fusion are examples of genetically modified APCs. APCs that are only pulsed are not genetically modified.

An "effective amount", as appearing in the present specification and claims, is an amount sufficient to effect beneficial or desired results. An effective amount can be administered in one or more administrations, applications or dosages. The vaccines of the present invention may be administered or applied transdermally, orally, subcutaneously, intramuscularly, intravenously or parenterally. For purposes of this invention, an effective amount of the vaccines is that amount which provokes an antigen-specific immune response in the subject. A suitable amount may be approximately 10×10⁶ cells for administration to one subject. An ampoule (which may be frozen and thawed before using) may contain 20×10⁶ cells. Cells form a frozen ampoule (or vial) may further be cultured again before administrated to a subject. Obviously the amount will be determined by the medical practitioner who will judge the nature and severity of the condition of the subject in need of treatment. The condition of the subject may also call for re-vaccination that may be performed at any time point after the first vaccination, e.g. each third to sixth week. Before administering the vaccine or the composition according to the present invention said vaccine or composition is preferably gamma-irradiated.

The term "an agent capable of removing sialic acid on cell surfaces", as appearing in the present specification and claims, refers to an agent that is capable of removing sialic acid from cell surfaces. Examples of such cells are the APCs as set out above. Agents which are capable of removing sialic acid from cell surfaces can be exemplified by neuraminidase (NAS) and antibodies raised against CD 43 (anti-CD43). Preferably said agent is NAS. NAS is thought to cleave the sialic acid from glyco-conjugates and anti-CD43 is thought to bring the sialic acid from the surface and into the cell. Other examples of said agents are genes coding for NAS or NAS-producing viruses or bacteria. The NAS may be obtained from bacteria and viruses e.g. from *Vibrio cholerae*, Newcastle virus, Influenza virus or *Clostridium perfringens*. A further preferred agent is an antibody against CD43, i.e. the CD43 membrane glycoprotein.

The term "culturing", as appearing in the present specification and claims, refers to the in vitro propagation of cells or organisms in media of various kinds. It is understood that the descendants of a cell grown in culture may not be completely identical (either morphologically, genetically, or phenotypically) to the parent cell. A suitable culturing medium can be selected by the person skilled in the art and examples of such media are RPMI medium or Eagles Minimal Essential Medium (EMEM).

A "subject", as appearing in the present specification and claims, is a vertebrate, preferably a mammal, more preferably a human. Mammals include, but are not limited to, murines, simians, humans, farm animals, sport animals, and pets. The subject may also be a patient.

An "antigen", as appearing in the present specification and claims, refers to any species, specimen or compound capable of eliciting an immune response e.g. tumor specimen, a tumor cell, a virus, a bacterium, a fungus, a parasite, a protein or a peptide. The tumor specimen may further be obtained from any tumor. According to a preferred embodiment of the present invention, the tumor specimen is selected to represent as many other tumor types as possible. If e.g. a vaccine against pancreatic cancer is desirable, then a representative specimen of pancreatic cancer (antigen) is used for the manufacture of a pancreatic cancer vaccine. If instead e.g. a vaccine against breast cancer is desirable, then a representative specimen of breast cancer (antigen) is used for the manufacture of a breast cancer vaccine. Said tumor specimen may further preferably be of allogeneic origin, but also autologous tumor specimens are thinkable for use in the present invention.

A "composition", as appearing in the present specification and claims, is intended to mean a combination of active agent, i.e. the vaccine, and another compound or composition, inert (for example, a detectable agent or label) or active, such as an adjuvant. In one particular aspect, a composition of this invention comprises the vaccine and a pharmaceutically acceptable carrier suitable for administration to the subject. A "pharmaceutical composition", as appearing in the present specification and claims, is intended to include the combination of an active agent with a carrier, inert or active, making the composition suitable for diagnostic or therapeutic use in vitro, in vivo or ex vivo.

As used herein, the term "pharmaceutically acceptable carrier", as appearing in the present specification and claims, encompasses any of the standard pharmaceutical carriers, such as a phosphate buffered saline solution, water, and emulsions, such as an oil/water or water/oil emulsion, and various types of wetting agents. The compositions also can include stabilizers and preservatives. For examples of carriers, stabilizers and adjuvants, see Martin, REMINGTON'S PHARM. SCI., 15th Ed. (Mack Publ. Co., Easton (1975)).

The terms "major histocompatibility complex" or "MHCI" refers to a complex of genes encoding cell-surface molecules that are required for antigen presentation to T cells and for rapid graft rejection. In humans, the MHC complex is also known as the HLA complex. The proteins encoded by the MHC complex are known as "MHC molecules" and are classified into class I and class II MHC molecules. Class I MHC molecules include membrane heterodimeric proteins made up of a chain encoded in the MHC associated non-covalently with β2-microglobulin. Class I MHC molecules are expressed by nearly all nucleated cells and have been shown to function in antigen presentation to CD8+ T cells. Class I molecules include HLA-A, -B, and -C in humans. Class I molecules generally bind peptides 8-10 amino acids in length. Class II MHC molecules also include membrane heterodimeric proteins. Class II MHC are known to participate in antigen presentation to CD4+ T cells and, in humans, include HLA-DP, -DQ, and DR. Class II molecules generally bind peptides 12-20 amino acid residues in length. The term "MHC restriction" refers to a characteristic of T cells that permits them to recognize antigen only after it is processed and the resulting antigenic peptides are displayed in association with either a self class I or self class II MHC molecule.

The isolation of an APC of step a) in the first aspect of the present invention may be performed in-vivo and/or in-vitro. The present invention thus provides a method for provoking antigen-specific immune responses, and in particular, immune responses against tumor antigens.

According to a further embodiment of the first aspect of the present invention there is provided a vaccine wherein said APC is an allogeneic monocyte, i.e. a monocyte derived from a second part (not derived from the same subject which is to be treated with the vaccine according to the present invention). In one aspect of the invention, the APCs, preferably monocytes, may be isolated from the white blood cell fraction of a mammal, such as a murine, simian or a human, preferably a human. The white blood cell fraction can be from the peripheral blood of the mammal, preferably a normal blood donor. This method includes the following steps: (a) providing a white blood cell fraction obtained from a mammalian source by methods known in the art such as leukapheresis; (b) separating the white blood cell fraction of step (a) into four or more sub-fractions by counter current centrifugal elutriation. Monocytes can also be recovered from PBMC by elutriation, Ficoll and Percoll gradients, through their ability to adhere to plastic or through negative or positive selection using antibodies linked to beads e.g. magnetic beads.

According to a further embodiment of the first aspect of the present invention there is provided a method comprising a further step between step a) and step b): cultivation of an APC, preferably a monocyte, or differentiation of an APC, preferably a monocyte, in a suitable medium into monocyte-derived DC, macrophage or macrophage-derived DC. This may be accomplished by incubating monocytes or myeloid leukemia cells in the presence of differentiation factors (growth factors) such as GM-CSF and/or IL-4 and/or TNF-alpha and/or macrophage colony forming factor (M-CSF) and/or IFN-gamma in different combinations.

According to a further embodiment of the first aspect of the present invention there is provided a method wherein the APC is an allogeneic monocyte or an in-vitro differentiated cell which is directly or indirectly derived from an allogeneic monocyte.

According to a further embodiment of the first aspect of the present invention there is provided a method wherein the antigen, as recited in step b), is a cancer antigen, preferably in the form of a soluble antigen, a tumor cell lysate or a viable tumor cell, all of allogeneic origin. According to a further embodiment of the first aspect of the present invention there is provided a method wherein step b) is performed through incorporating the antigen within the APC using any one of the following methods: pulsing with soluble antigen or tumor cell lysate, transfection with genes coding for the antigen or fusion with an allogeneic tumor cell. As a result there is provided a vaccine adapted for use against cancer. Also a mixture of different cancer antigens may be used.

According to a further embodiment of the first aspect of the present invention there is provided a method wherein the agent capable of removing sialic acid from the cell surface of the APC, as recited in step c), is neuraminidase (NAS), one or more genes coding for neuraminidase or neuraminidase-producing viruses or bacteria; or an antibody against CD43.

According to a further embodiment of the first aspect of the present invention there is provided a method wherein the treatment of step c) is performed by any of the following methods: treating the APC with NAS, transfecting the APC with genes coding for NAS or infecting the APC with NAS-producing viruses or bacteria as recited above. Preferably the APCs may be transfected with NAS after modification, e.g. transfection, with the antigen as set out above earlier.

According to a further embodiment of the first aspect of the present invention there is provided a method comprising an additional step in which the APC is exposed to hyperthermia (heat stress) during step b) or between steps b) and c).

According to a further embodiment of the first aspect of the present invention there is provided a method wherein the hyperthermia recited above is performed at a temperature of from 39 to 42° C. and during from 2 to 6 hours. This heat stress is preferably performed at a temperature of from 39 to 42° C. during approximately 3 hours. Preferably pulsing, i.e. one way of modifying the APCs, is performed at the same time i.e. in parallel.

According to a further embodiment of the third aspect of the present invention there is provided a frozen container (such as a test tube, an ampoule or a vial) comprising a composition according to the third aspect.

According to a further embodiment of the fourth aspect of the present invention there is provided therapeutic use of an effective amount of a vaccine according to the second aspect of the invention or a composition according to the third aspect of the invention.

According to a further embodiment of the fourth aspect of the present invention there is provided a vaccine according to the first aspect for medical use.

According to a further embodiment of the fourth aspect of the present invention there is provided use of a vaccine according to the first aspect for the manufacture of a medicament for use against cancer.

An explanation to the unexpected effect, which the present inventors are not bound to in any way, of the present invention might be that the allogeneic modified APCs, preferably monocytes, when injected into a subject generally induces a local MLR which creates an environment which is favorable for recruitment and maturation of DC-precursors which during their differentiation/maturation also acquire e.g. tumor-derived peptides from locally lysed allogeneic hybrid-cells i.e. modified APCs. Thus the normally negative effect induced by a transplanted or transfused allogeneic APC (allo-immunization) can be used in a positive way e.g. immunization against other foreign antigens such as cancer antigens.

For an immunologist/a person skilled in the art the concept of the present invention is completely different from the technique disclosed in WO 9421798, i.e. the supplying of tumor antigens within a NAS-treated but MHC-incompatible allogeneic APC, is completely different from the technique disclosed in WO 9421798 where MHC-compatibility between the NAS-transfected APC and T cells is a prerequisite. For the person skilled in the art our concept may even prima facie appear as lunacy (even if the APC would be NAS-treated). This would be the case if the present strategy of the present invention departed from the hypothesis that the NAS-treated allogeneic APC would be able to present the tumor antigen for the tumor specific T cell of the recipient. It is thus an immunological matter of course that in WO 9421798 they have not included allogeneic APC as thinkable APC. The present concept of the present invention on the contrary is based upon using NAS-treated allogeneic APCs as "carriers" of tumor antigen and at the same time an adjuvant which within the recipient commences an inflammatory reaction (of the same type but very likely stronger than the one leading to priming of alloreactive T cells after transplantation of allogeneic organs) which initially is not tumor specific.

The allogeneic APCs of the present invention are thus not intended for presenting the tumor antigen for the recipients T-cells self. On the contrary they operate as an adjuvant through the induction of one, without regarding the tumor, unspecific activation (alloactivation) of the recipients immune system. This in turn leads to that they themselves become lysed (via activation of alloreactive T cells/NK cells) so that their contents of tumor antigen become accessible for APCs of the recipients which due to the inflammatory process have been recruited to the vaccination area.

Patent application US 20020039583 includes antigen-"loaded" allogeneic APCs (and xenogeneic APC) as potential cellular components of a cellular vaccine. However the inventors appear to believe that T cells recognize peptide/protein/immune complexes which are located on a cell surface without necessity of self MHC-restriction. Apparently not even an APC is necessary as the inventors believe that a non-cell-associated complex may also stimulate T cells (see page 13, right column "T cells may be stimulated with stress protein complexes, polynucleotide encoding a stress protein complex and/or and antigen presenting cell (APC) that express such a stress protein complex"). It is never mentioned that an allogenic APCs would be capable of operating as an adjuvant in order to commence an immunologic reaction that would lead to the recruitment of the patients (the subjects) own APCs. For a person skilled in the art it must appear unlikely that the use of antigen-"loaded" allogeneic APCs, as set out in US 2002' would lead to a direct activation of MHC-incompatible T cells. Further, it appears even more unlikely that a person skilled in the art would combine this concept with the NAS-concept disclosed in WO 9421798.

When comparing the technique disclosed in Chang E. Y. et al, (International Journal of Cancer, 2000, Vol 86. No. 5, pp 725-730), one of the aims therein is the same as in the present invention, namely the recruitment of the patients APC to the vaccination site. In the concept of the present invention we additionally obtain production of chemokines such as MIP-1 alpha and RANTES, recruiting monocytes/immature DCs and maturating factors such as IL-1 beta, IL-6, TNF-alpha and TH-1 controlling IFN-gamma (see the accompanying figures of the present specification).

Preferred features of each aspect of the invention are as for each of the other aspects mutatis mutandis. The prior art documents mentioned herein are incorporated to the fullest extent permitted by law. The invention is further described in the following examples in conjunction with the appended drawings, which do not limit the scope of the invention in any way. Embodiments of the present invention are thus described in more detail with the aid of examples of embodiments and figures, the only purpose of which is to illustrate the invention and are in no way intended to limit its extent.

EXAMPLES

Example 1

Preparation of Monocytes from Leukocytes

Monocytes may be obtained using peripheral blood of a human. This method includes the following steps: (a) providing a white blood cell fraction obtained from a human source through leukapheresis; (b) separating the white blood cell fraction of step (a) into four or more sub fractions by counter current centrifugal elutriation. Monocytes can also be recovered from PBMC by elutriation, Ficoll and Percoll gradients or through their ability to adhere to plastic. Negative selection of monocytes using magnetic beads linked to certain antibodies available from Dynal or Miltenyi is also possible.

Modification of Monocytes

Figure 1:
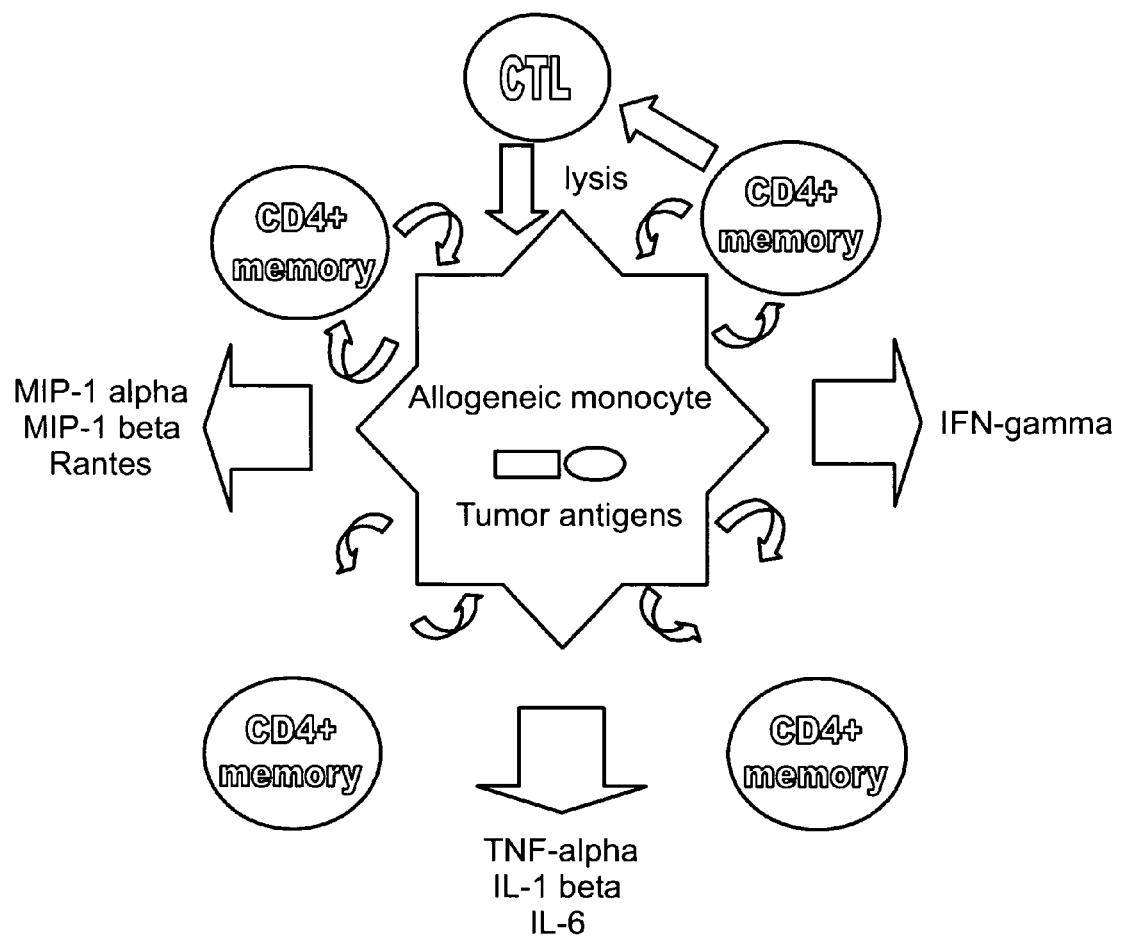
FIG. 1 illustrates allogeneic monocytes as carriers of tumor antigens.
Figure 2:
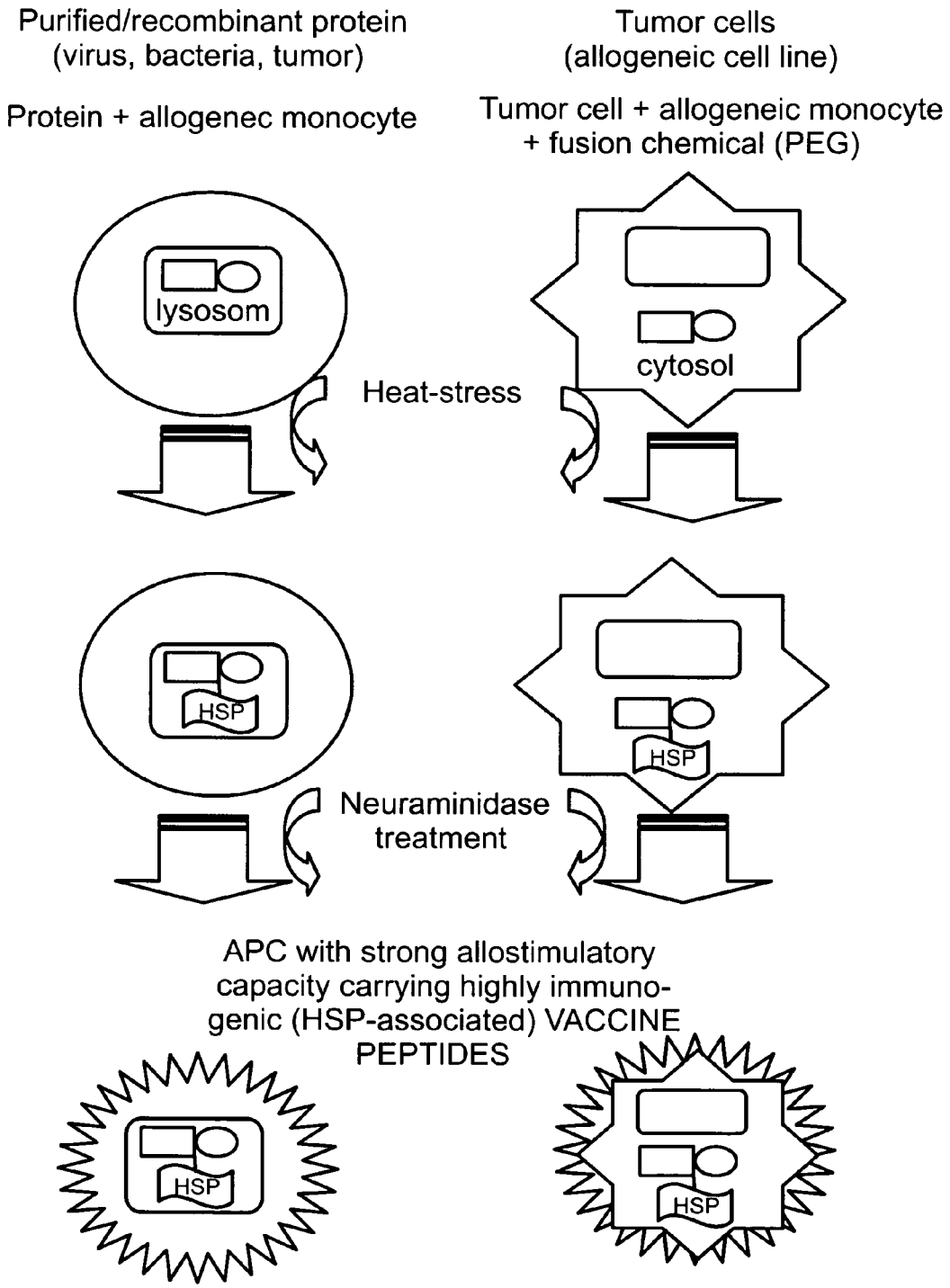
FIG. 2 illustrates the vaccine concept of the present invention.

The monocytes may then undergo pulsing treatment whereby the monocytes are treated (incubated) in a solution with pure soluble tumor protein (antigen) at a protein concentration of 1-10 mg/ml during 3 hours at 37° C. Pulsing may also be used when the antigen is tumor cell lysates obtained e.g. from a) repeated heat—thawing or b) sonication both with subsequent centrifugation. Then the protein concentration in the supernatant is measured and adjusted to 100-200 µg/ml. Monocytes may further be fused (whereby using PEG, i.e. polyethylene glycol, as fusion chemical; the PEG solution is preferably 50% and is diluted subsequently) with tumor cells thus creating immortalized cells (hybrids) and thus vaccines. The fusion is performed between allogeneic tumor cells and allogeneic monocytes from a second part (see further below) Transfection with genes coding for antigens may also be used to create modified monocytes i.e. vaccines. (see FIG. 1 and 2).

Neuraminidase (NAS) Treatment

The modified monocytes may be treated with 25 mU/ml of NAS. The NAS treatment has been shown to increase most of the chemokines/cytokines (see FIG. 3). The monocytes may also be pre-transfected with a suitable gene coding for a NAS e.g. from *V. cholerae*.

Figure 3:
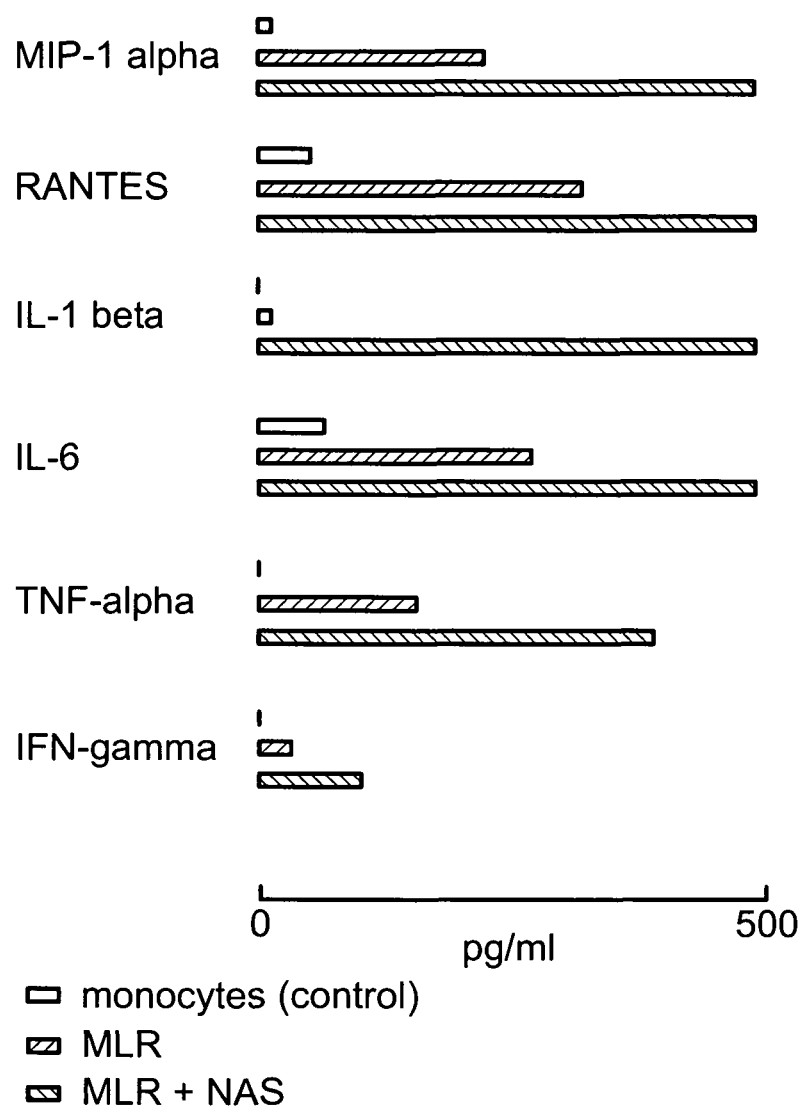
FIG. 3 illustrates the results of the pretreatment using neuraminidase (NAS).
Figure 4:
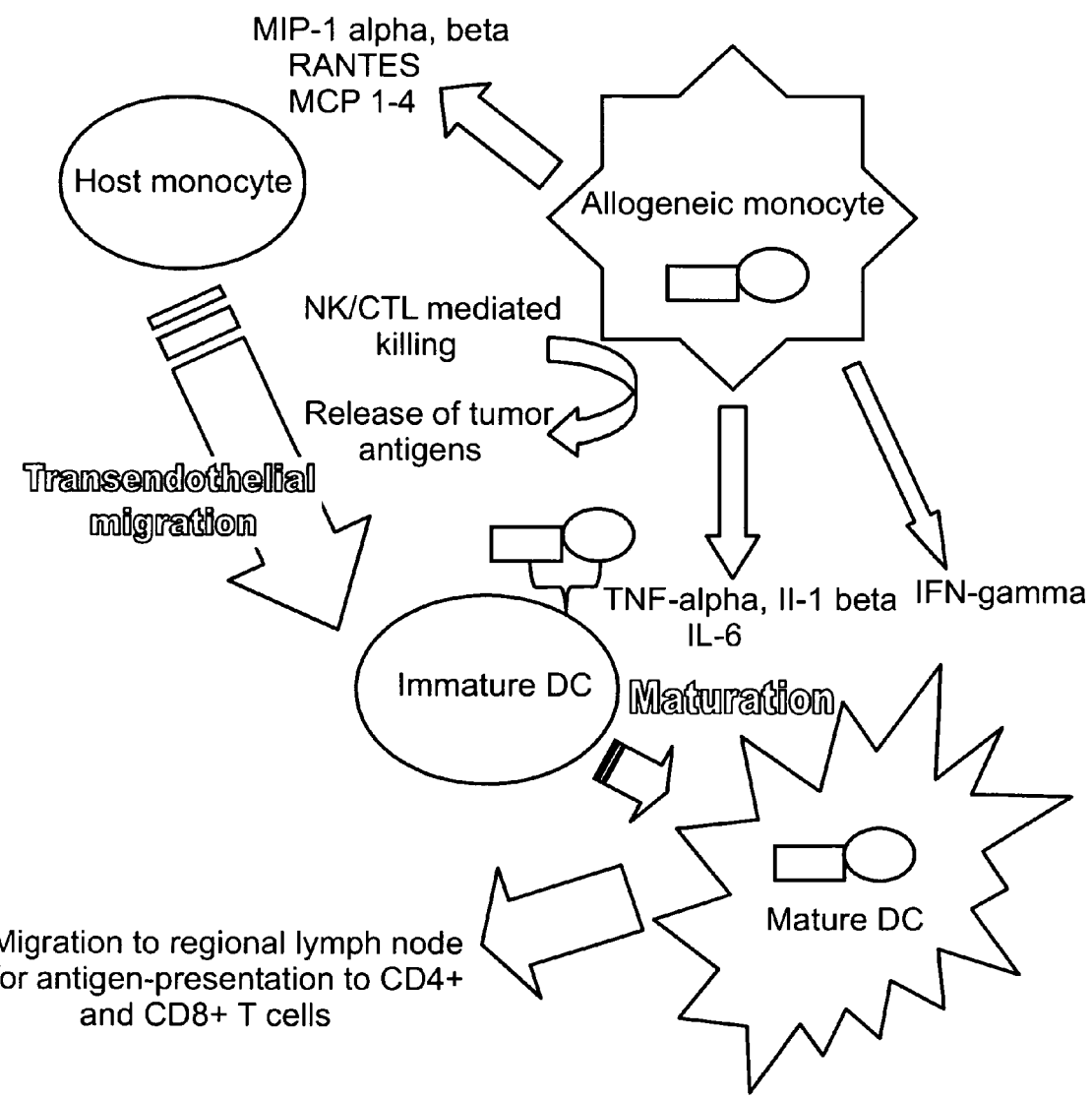
FIG. 4 shows an optimum formula for in vivo propagation of mature DCs carrying phagocytosed tumor antigens, i.e. one preferred embodiment of the present invention.

Effect of neuraminidase (NAS)-treatment on direct allorecognition and on chemokine/cytokine production It has been known for over a decade that treatment of stimulator APC with neuraminidase, which leads to the removal of sialic acid on the cell membrane, significantly enhance their capacity to stimulate allogeneic T cells in an allogeneic MLR. It has been suggested that increased intercellular adhesiveness induced by decreased cell-surface charge is a likely cause of this neuraminidase effect. It has also been suggested that neuraminidase treated APC might provide some unidentified accessory factor required by T cells for activation. It has now been observed that allogeneic peripheral blood mononuclear cells (PBMC) treated with NAS from *Vibrio cholerae* (25 mU/mL) induce a stronger proliferative response among responder T cells in a one-way MLR than untreated PBMC. Moreover, by measuring chemokine and cytokine production during a one-way allogeneic MLR it was discovered that MIP-alpha, RANTES, IL1-beta, TNF-alpha and IFN-gamma are produced in several-fold higher amounts when the stimulator cells (irradiated monocytes) have been treated with NAS (FIG. 3)

Hyperthermia

Hyperthermia (heat stress treatment) of modified cells may be performed by subjecting the modified monocytes to heating at 40° C. during 3 hours. The fever treatment has further been shown to upregulate the amount of HSP-coupled tumor antigen (in the lysosome and/or in the cytoplasm) within the monocytes. This treatment has also been shown to increase the amount of immunogeneic tumor peptides. The presentation is not negatively affected.

The effect of heat stress on direct allorecognition Cytosolic as well as lysosomal proteins are known to be associated to heat shock proteins (HSP) during heat stress and it is well established that HSP associated peptides become more immunogenic in vivo. This is likely due to a more efficient uptake by DC (receptor-mediated endocytosis/phagocytosis). Moreover certain HSPs have been shown to induce maturation of immature DC in vitro. It has been found that a mild hyperthermic stress (41° C. for 2 hours), known to induce a substantial up-regulation of cellular HSP-expression, do not negatively affect the stimulatory capacity of irradiated PBMC to induce allogeneic T cells responses as determined by proliferation in a one-way MLR (data not shown)

Phenotypical Studies by FACS and Cytokine/Chemokine Measurements

Figure 5:
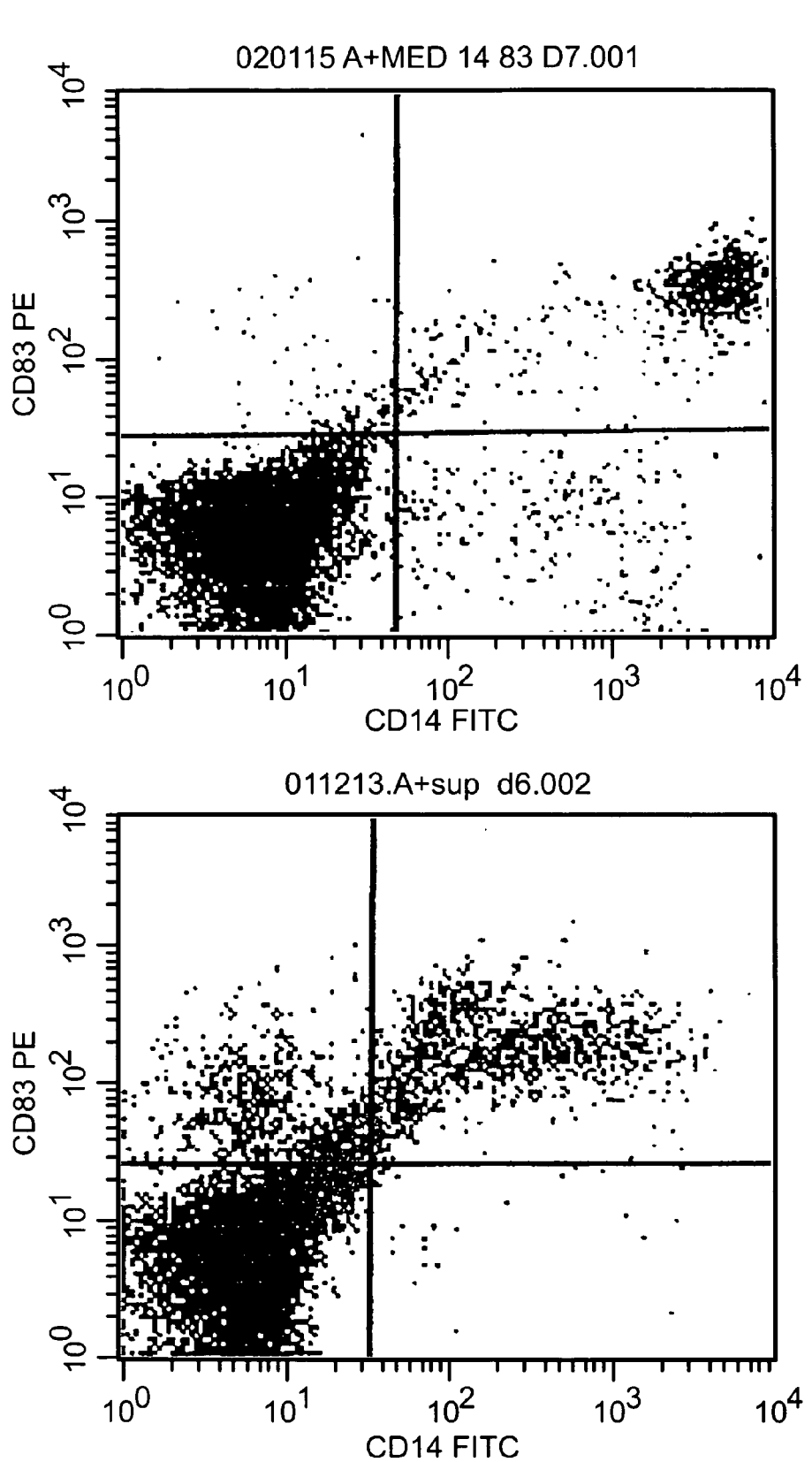
FIG. 5 shows that monocytes cultured in media containing 50% (v/v) MLR conditioned media (MLR-CM) develop into CD83+ cells with low expression of CD14 after 6 days (lower graph). The upper graph depicts a control experiment without addition of MLR-CM.
Figure 6:
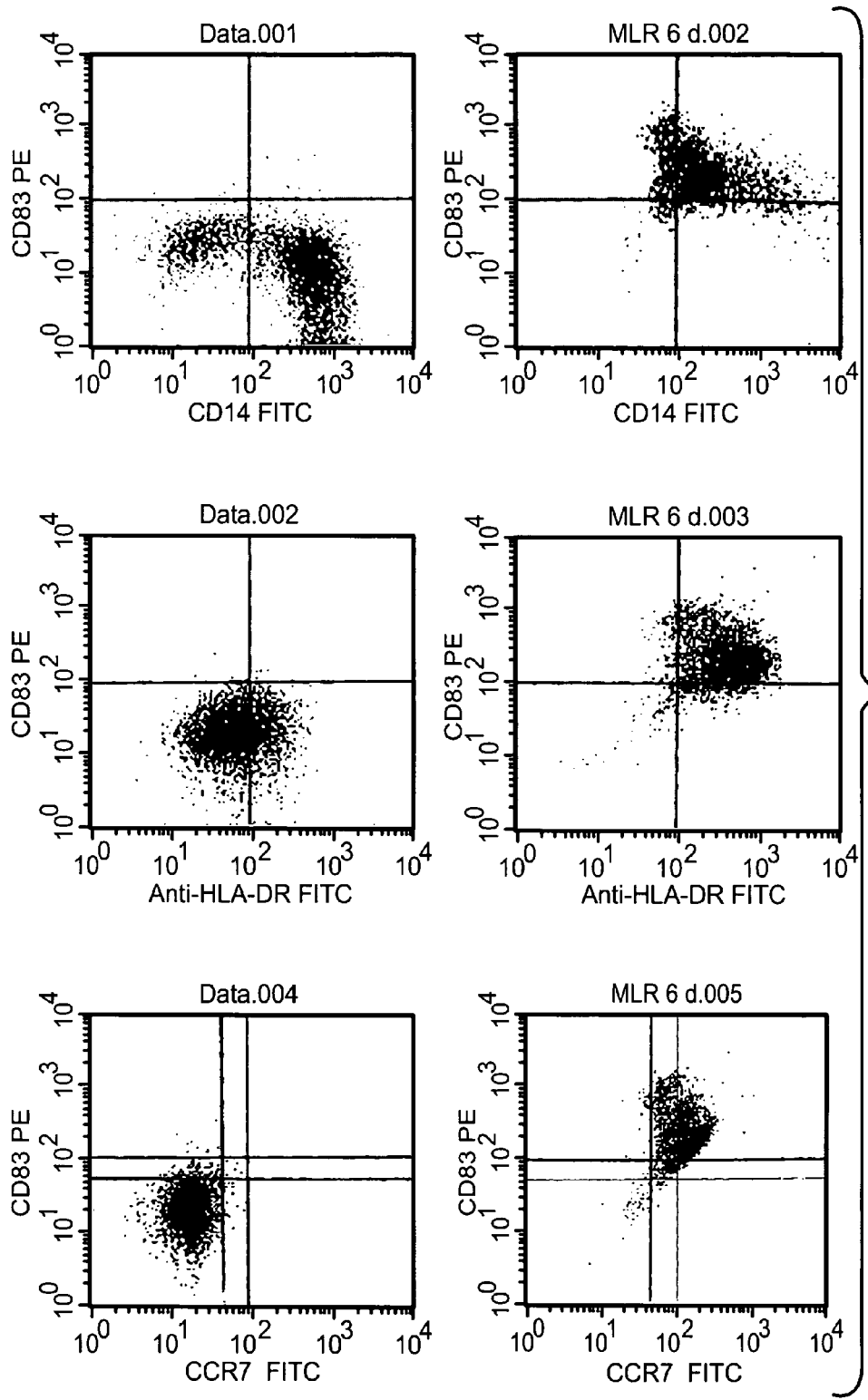
FIG. 6 shows that MLR-CM (50 v/v %) induce a phenotypical maturation (CD14 low, CD83+, CD86+, HLA-DR+ and CCR7+) of monocyte-dervied immature DCs as illustrated in the graphs to the right. The graphs to the left depict the cellular phenotype of untreated monocytes.
Figure 7:
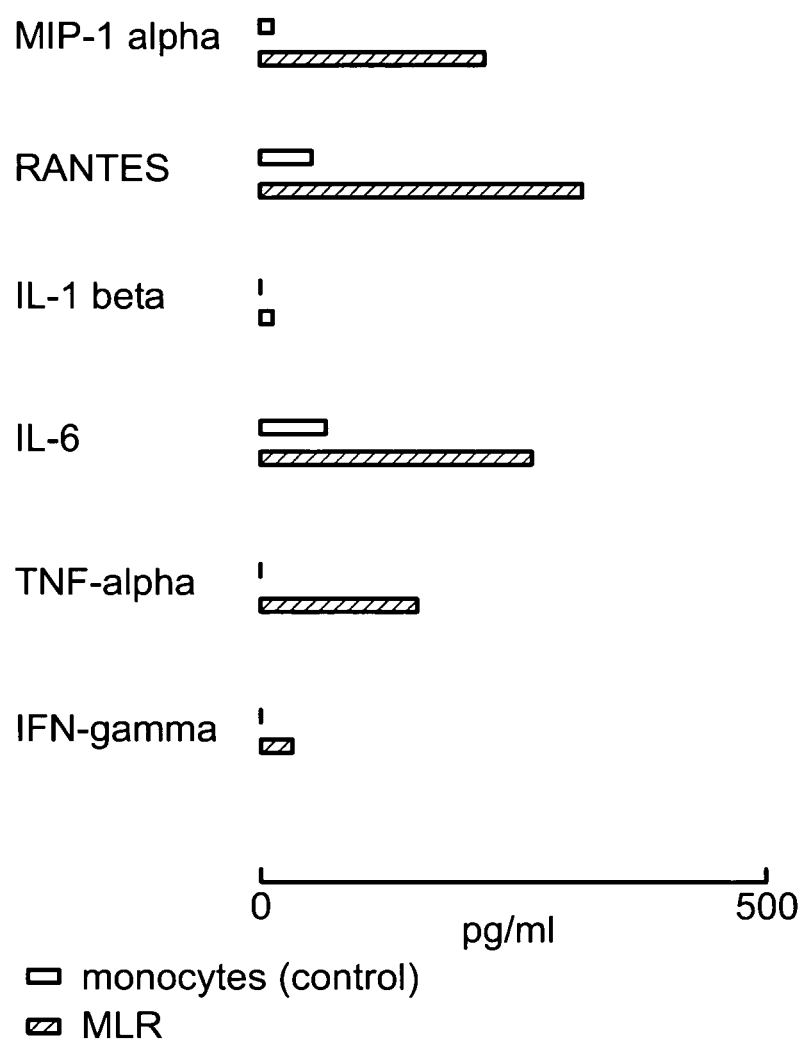
FIG. 7 shows the cytokine profile determined in an MLR-CM using Luminex.

Earlier studies by others have shown that monocyte conditioned medium (supernatants taken from monocyte cultures activated by their Fc-receptors) as well as T-cell conditioned medium (supernatants taken from T cell cultures activated by stimulation with anti-CD3 antibodies) efficiently induce DC maturation. Our hypothesis was that the immune interaction between allogeneic monocytes and responder T cells leads to the production of a chemokine/cytokine "cocktail" that also could induce a final maturation of immature DC in vitro. Through performing primary phenotypic studies during a traditional MLR an interesting phenomenon was discovered. During a so-called one-way MLR (irradiated stimulator cells) but not during two-way MLR or during stimulation with nectrotic or apoptotic allogeneic monocytes a subpopulation of CD83 positive cells with low expression of CD14 but high expression of CD86 and HLA-DR was found. By adding MLR-CM (50% v/v) taken at day 6 from one-way allogeneic MLRs using irradiated plastic-adherent mononuclear cells as stimulators ($1 \times 10^5$ cells/ml) and allogeneic PBMCs ($1 \times 10^6$ cells/ml) to adherent monocytes in culture medium it was further observed that these "bystander" cells developed a similar phenotype (CD83+/CD14 low) after 6 days as illustrated in FIG. 5. MLR-CM (50 v/v %) were then added to immature, monocyte-derived DCs (differentiated in GM-CSF/IL4 for 6 days). Two days later (day 8), the cells where phenotyped by FACS. It was found that the monocytes had differentiated into phenotypically fully mature DCs as illustrated in FIG. 5 where the graphs to the left depict the cellular phenotype at day 0 and the graphs to the right depict the phenotype at day 8. Of particular interest is that a high expression of CCR7 could be shown on these mature DCs which is of central importance for the migration to regional lymphatic glands. By using a multi-analyte profiling technique (Luminex) the cytokine profile was determined in an MLR-CM and several cytokines with known effect on monocyte differentiation and maturation of DCs were found including TNF-alpha, IFN-gamma, IL-1 beta. The results are depicted in FIG. 7. Additionally several chemokines are produced including MIP-1 alpha. Through pre-treatment of the stimulatory cells with neuraminidase (NAS) from *Vibrio cholerae* an additional increase of the chemokine/cytokine production in a MLR was achieved (see FIG. 3).

To conclude, the above discovery could well explain why viable passenger APCs are so important for the allo-immunization. The preformed T-cell reactivity against directly presented allo-antigen on these cells thus leads to a favourable environment for recruitment and local maturation of DCs of the transplanted individual. This accumulation and maturation of DCs is a favourable prerequisite for a subsequent efficient priming of naive alloreactive T-cells (which recognizes allopeptides via the indirect route) in secondary lymphoid organs.

Establishment of monocytoma cell lines by fusion of human cancer cell lines with allogeneic peripheral blood monocytes Human tumor cell lines (TCLs) including the breast cancer cell line MCF7 and the prostate cell line DU 145, purchased from the American Tissue Culture Collection, may be used. The TCLs may be cultured in RPMI 1640 medium supplemented with 10% heat-inactivated human AB serum, 2 mM L-glutamine, 100 U/mL penicillin, and 100 microgram/mL streptomycin until fusion. Isolated allogeneic peripheral blood monocytes from healthy blood donors may be incubated with the TCL for 5 minutes at a ratio of 10:1 in serum-free RPMI 1640 medium containing 50% polyethylene glycol (PEG). RPMI 1640 is then added slowly to dilute the PEG. After washing and elimination of unfused cells by density gradient the monocytomas may be resuspended in RPMI 1640 medium supplemented with human AB serum, L-glutamine, penicillin and streptomycin as stated above.

Selection of monocytoma cell lines from non-hybrid cells The generation of cell hybrids may be conducted in analogue with the generation of hybridomas producing monoclonal antibodies. This relies on that the HGPRT can be fused for both positive and negative selection. At a first, 6-thioguanine may be used to select cancer cell lines that have mutated the HGPRT gene. This chemical is converted to a toxic intermediate by the HGPRT gene product. The mutated cells are subsequently fused to monocytes/dendritic cells using PEG or electrofusion, and when grown in HAT media only fused cells will survive. This is due to that HAT media will kill the cancer cells lacking the HGPRT gene and that monocytes/dendritic cells are not long-lived in culture although they have an active gene, In vitro priming of human Th1 cells against tumor antigens The ability of a primary allogeneic MLR to induce a substantial priming of antigen-specific human CD4+ Th1 cells may be assessed a follows:

Monocytes may be pulsed with either soluble tumor proteins (1-10 mg/mL for 3 hours) including prostatic soluble antigen (PSA) and cancer antigen (CA)-125 or repeatedly freeze-thawed tumor cell lysates (100-200 microgram cancer cell protein/mL for 3 hours) from tumor cell lines including breast cancer and prostate cancer cells. After washing and gamma-irradiation the pulsed monocytes may be used as stimulator cells in a primary MLR using allogeneic PBMC as responders. After 6 days the cell culture may be washed and replaced into fresh culture medium containing 10 U/mL interleukin (IL)-2. Two days later the cells from the primary MLR may be restimulated by adding irradiated PBMC, autologous to the responder cells in the primary MLR, pulsed with the antigen that was used during the primary MLR. The number of CD4+ Th1 cells that were primed during the primary MLR can then be recorded 1-2 days later by using an ELISPOT assay specific for IFN-gamma producing cells.

Using the same assay principle the ability of allogeneic monocytomas to prime CD4+ Th1 cells during a primary MLR can be studied after restimulation with autologous PBMC pulsed with a cell lysate from the monocytoma used in the primary MLR.

Comparison with Prior Art Techniques

A comparison was made with the prior art techniques disclosed in WO 9421798 and Chang E. Y. et al, (International Journal of Cancer, 2000, Vol 86. No. 5, pp 725-730.

Figure 8:
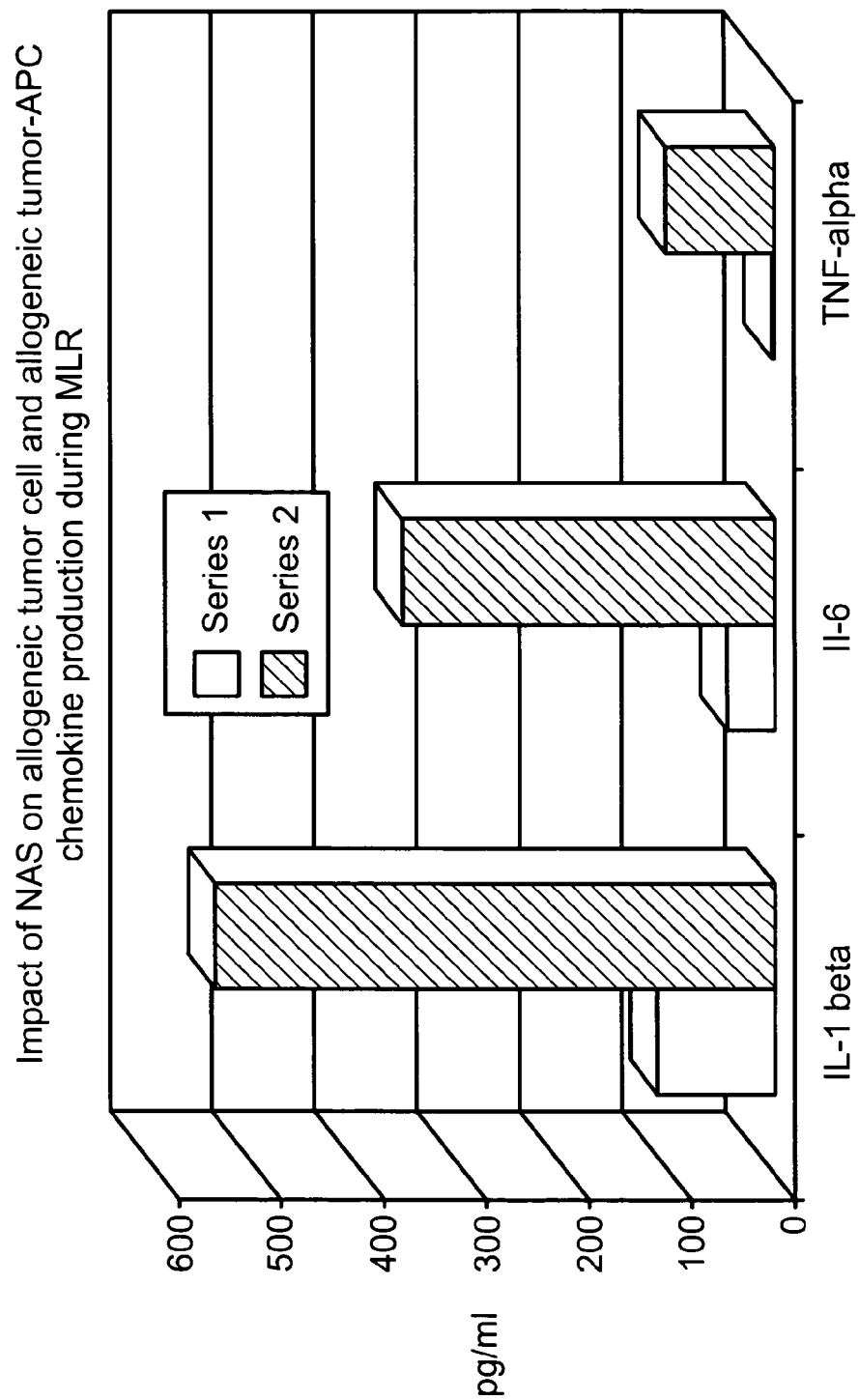
FIG. 8 shows the impact of NAS on allogeneic tumor cell and allogeneic tumor-APC chemokine production during MLR.

In Chang et al it is described that through injecting tumor cells which produces GM-CSF they try to induce an inflammatory environment which leads to the recruitment of the patients own APC to the site of the vaccination (further studies around the effect of GM-CSF have shown that local GM-CSF production induces MIP-1 alpha production which could explain the observed recruitment of immunological cells, including APC to the vaccination site). As these GM-CSF-producing tumor cells are not intended to operate self as APC for tumor specific T cells you may use autologous as well as allogeneic tumor cells as antigen source. A precondition is however that they contain the same tumor antigen which is expressed in the tumor of the patient. The selection of allogeneic tumor cells in Chang et al is essentially of pure practical nature even though they mention that allogeneic vaccines (i.e. vaccines which comprises allogeneic tumor cells, not APC) may give a better immune response compared with autologous tumor cell vaccines (not APC). The obtained vaccine effect in the study of Chang E. Y. et al are essentially not to be ascribed, according to the authors, to that the tumor cells were allogeneic (most of the tumors are not comprised by APC-derived cells and thus they miss MHC class II which is the most important component in order to induce an inflammatory reaction against allogeneic cells) but to their capability to produce GM-CSF. In their publication there was also a formal comparison done between immunogenicity of allogeneic tumor cells (B16E7) and GM-SCF producing B16E7 cells (B16GME7). The result disclosed shows clearly that allogeneic tumor cells which do not produce GM-SCF have a minimal vaccination effect in comparison with GM-CSF producing cells. These findings corresponds with results which we now have obtained in vitro through comparing the inflammatory reaction (chemokine/cytokine production) which arises when mixing immune cells (mononuclear cells from peripheral blood) with allogeneic tumor cells (THP1 cells which comprises precursors of monocytes) or allogeneic APC (THP1 cells which via culturing in GM-CSF and IFN-alpha differentiated out to functional APC), see FIG. 8. Allogeneic tumor cells (including precursors to APC as THP-1 cells) thus appear to be weak immune stimulators if they are compared with fully matured allogeneic APC. Which can be seen in FIG. 8, NAS-treatment of allogeneic APC leads to a further strong increase in chemokine/cytokine production. We have in an in-vitro model observed that the inflammatory reaction which arises when a potent APC (the vaccine component) is brought into contact with allogeneic mononuclear cells (corresponds to immune cells of the patient), then, besides MIP-1 alpha, several other chemokines with well known ability of recruiting APC are produced. Additionally, several pro-inflammatory cytokines are produced, with well known ability to additionally make recruited immature DCs to develop into fully mature DCs (neither GM-CSF nor MIP-1 alpha have the ability for this). Through incubating immature DCs with medium from the above reaction we have also been able to show that this medium really induces a DC maturation. Finally, through pre-treating allogeneic APCs with NAS we have observed that chemokine- and cytokine-production multiplies in the above model.

Figure 9:
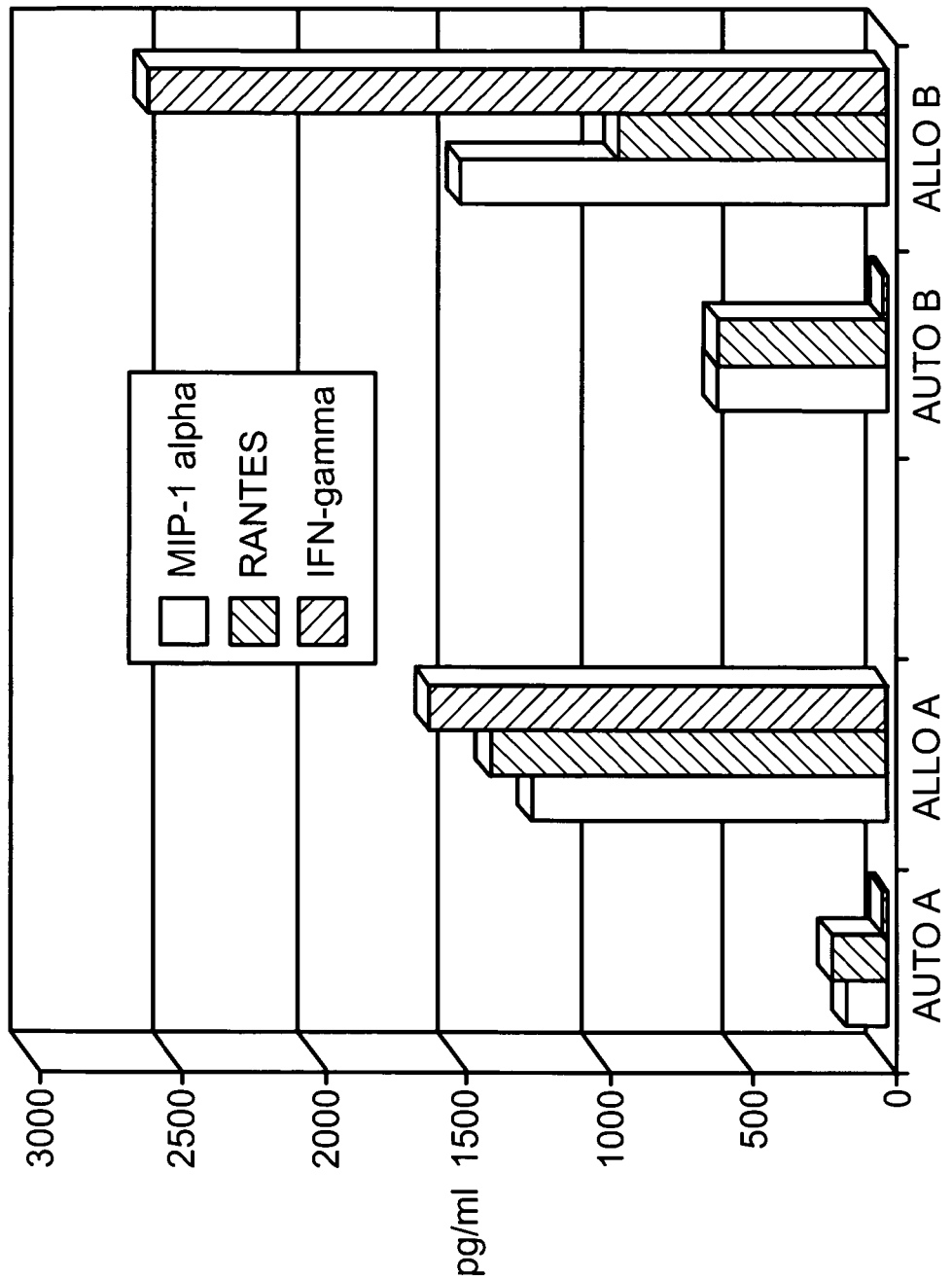
FIG. 9 shows chemokine and cytokine production in autologous vs allogeneic MLR, using NAS-treated stimulator APCs.

Further we studied if there were any difference between NAS-treated autologous and allogeneic APCs regarding the induction of inflammatory chemokines and och cytokines. In a comparative study, the concept of WO 9421798 was used in comparison (with the present invention), wherein the inventors in WO 9421798 got a vaccine effect. In our comparative study (see FIG. 9) it was shown that NAS-treated APCs induce a more powerful inflammatory response of allogeneic responder cells in comparison with autologous responder cells. Which is apparent from FIG. 9 (Auto A, Auto B represent autologous MLR, Allo A and Allo B represent allogeneic MLR) is that above all the IFN-gamma production is influenced (an approximately 100 times more powerful production in the allogeneic situation). In addition we have observed that NAS-treated APCs normally induce 50 to 100-times stronger proliferation of allogeneic responder cells than autologous. As IFN-gamma is one of the most important cytokines in order to control the immune response against a so called TH1-response, a response which you aim for during cancer vaccination, the potential of our vaccine-concept is even more apparent. As also can be seen is that allogeneic tumor cells in themselves are poorly immunogenic (see FIG. 9). An indication of an assessable activation in vitro of allogeneic responder cells could not be found, not even if the "stimulating" tumor cells were NAS-treated. If on the other side the tumor cells are comprised by fully matured APCs then NAS-treatment leads to a very powerful inflammatory response with the production of several of the above mentioned cytokines and chemokines.

The Impact of NAS-treatment on Different APCs as to CC Chemokine Production

Figure 10:
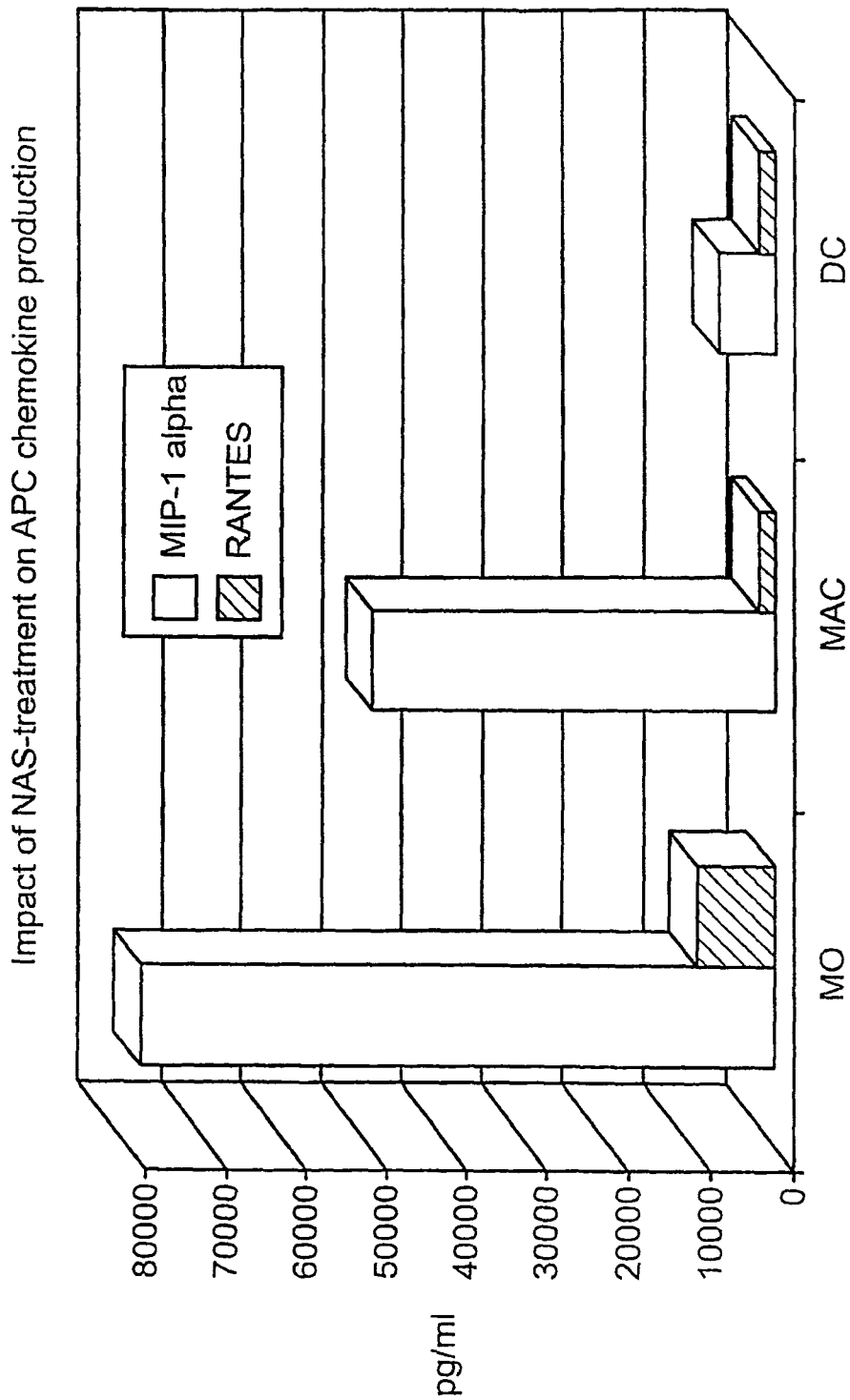
FIG. 10 shows the impact of NAS-treatment on APC chemokine production.

It has been reported that immature DCs produce higher levels of CC chemokines than mature DCs upon stimulation with lipopolysaccharide and that macrophage-derived DCs are more potent than monocyte derived DCs in this aspect. We have compared freshly isolated monocytes with macrophages (monocytes differentiated in M-CSF media for 7 days) and immature DCs (monocytes differentiated in GM-CSF+ IL-4 for 7 days) and found that monocytes were more potent than macrophages or DCs to produce CC chemokines upon NAS-treatment (1×106 cells/ml stimulated with *Vibrio cholerae* neuraminidase 25 mU/ml for 24 hours). These findings are illustrated in FIG. 10.

Figure 11:
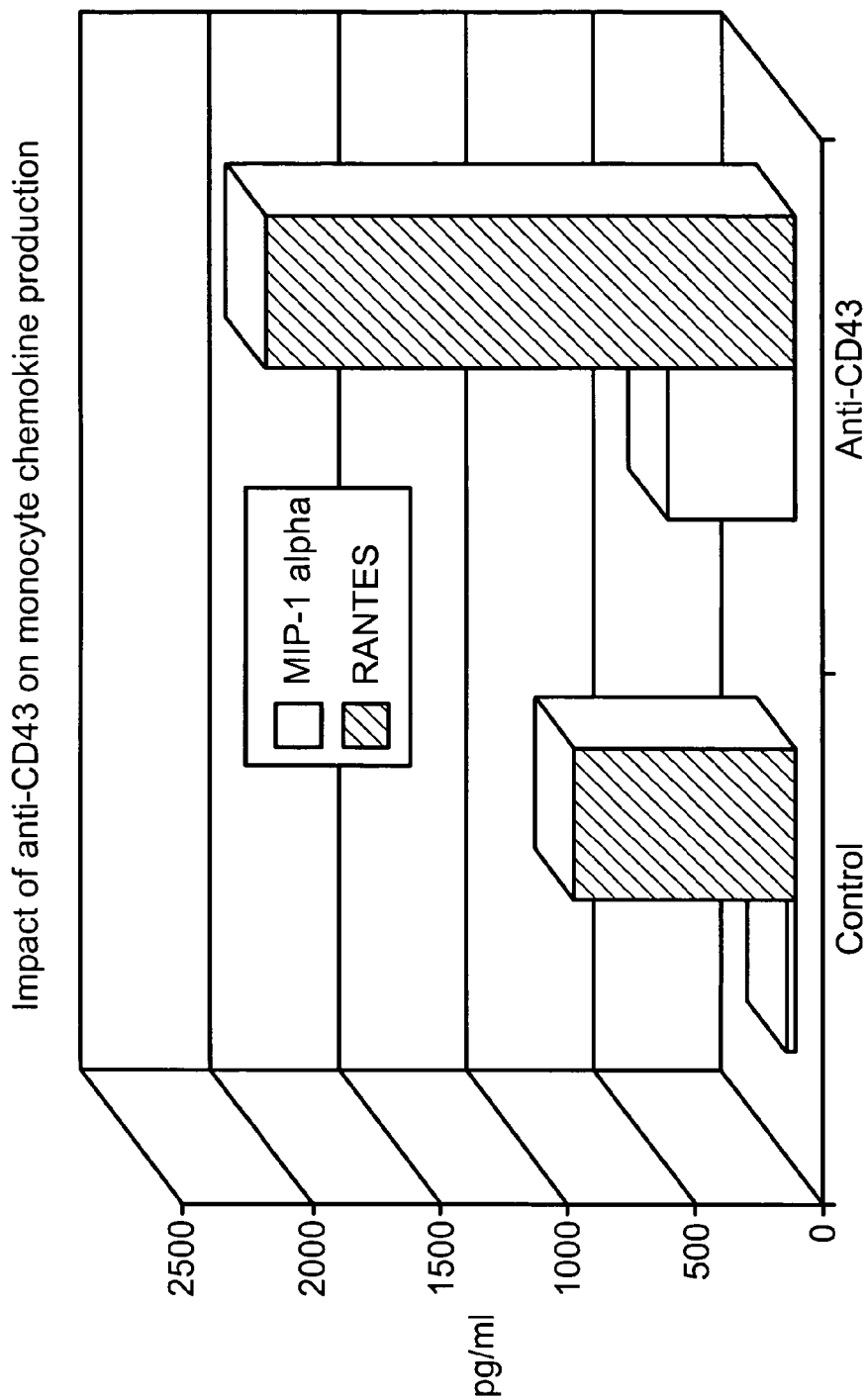
FIG. 11 shows the impact of anti-CD43 on monocyte chemokine production.

The effect of anti-CD43 on monocyte chemokine production Treatment of monocyte-derived dendritic cells with antibodies against the CD43 membrane glycoprotein have been shown to down-regulate sialic-acid expression on the cell membrane and to induce production of pro-inflammatory cytokines such as IL1-beta, Il-6 and TNF-alpha. We have studied the impact of anti-CD43 on monocyte chemokine production and found that anti-CD43 also induce a substantial production of chemokines which is illustrated in FIG. 11.

Various embodiments of the present invention have been described above but a person skilled in the art realizes further minor alterations, which would fall into the scope of the present invention. The breadth and scope of the present invention should not be limited by any of the above-described exemplary embodiments, but should be defined only in accordance with the following claims and their equivalents. For example, any of the above-noted compositions and/or methods can be combined with known therapies or compositions. Other aspects, advantages and modifications within the scope of the invention will be apparent to those skilled in the art to which the invention pertains.

The invention claimed is:

1. A method for inducing an antigen-specific immune response to treat cancer in a subject, said method comprising:
   administering an effective amount of a cellular allogeneic fully MHC-incompatible immunogenic composition to a subject in need thereof, wherein said allogeneic fully MHC-incompatible immunogenic composition is a fully MHC-incompatible monocyte-derived dendritic cell pulsed with a soluble cancer antigen or a tumor cell lysate comprising a cancer antigen.

2. The method according to claim 1, wherein the cancer antigen is a soluble antigen.

3. The method according to claim 1, wherein the cancer antigen is from a tumor cell lysate.

4. The method according to claim 1, wherein the cancer antigen is from a viable tumor cell.

5. The method according to claim 1, wherein the cancer antigen is of allogeneic origin.

6. The method according to claim 1, wherein the sialic acid has been removed from the surface of said monocyte-derived dendritic cell.

7. A method for inducing an antigen-specific immune response in a subject, said method comprising:
   administering an effective amount of a cellular allogeneic fully MHC-incompatible immunogenic composition to a subject in need thereof, wherein said allogeneic fully MHC-incompatible immunogenic composition is a fully MHC-incompatible monocyte-derived dendritic cell pulsed with a soluble cancer antigen or a tumor cell lysate comprising a cancer antigen.

8. The method according to claim 7, wherein the cancer antigen is a soluble antigen.

9. The method according to claim 7, wherein the cancer antigen is from a tumor cell lysate.

10. The method according to claim 7, wherein the cancer antigen is from a viable tumor cell.

11. The method according to claim 7, wherein the cancer antigen is of allogeneic origin.

12. The method according to claim 7, wherein the sialic acid has been removed from the surface of said monocyte-derived dendritic cell.

13. A method for treating cancer in a subject, said method comprising:
   administering an effective amount of a cellular allogeneic fully MHC-incompatible immunogenic composition to a subject in need thereof, wherein said allogeneic fully MHC-incompatible immunogenic composition comprises an effective amount of a fully MHC-incompatible monocyte-derived dendritic cell pulsed with a soluble cancer antigen or a tumor cell lysate comprising a cancer antigen.

14. The method according to claim 13, wherein the cancer antigen is a soluble antigen.

15. The method according to claim 13, wherein the cancer antigen is from a tumor cell lysate.

16. The method according to claim 13, wherein the cancer antigen is from a viable tumor cell.

17. The method according to claim 13, wherein the cancer antigen is of allogeneic origin.

18. The method according to claim 13, wherein the cancer antigen is from a breast tumor cell.

19. The method according to claim 13, wherein the cancer antigen is from a prostate tumor cell.

20. The method according to claim 13, wherein the sialic acid has been removed from the surface of said monocyte-derived dendritic cell.

* * * * *